US008092434B2

(12) United States Patent
Harlan et al.

(10) Patent No.: US 8,092,434 B2
(45) Date of Patent: Jan. 10, 2012

(54) DEVICE AND METHOD FOR WASHING NASAL PASSAGES

(75) Inventors: Jeffrey Harlan, Corona, CA (US);
Diane Heatley, Madison, WI (US);
David Gallo, San Diego, CA (US)

(73) Assignee: Med-Systems, Inc., Madison, WI (US)

( * ) Notice: Subject to any disclaimer, the term of this patent is extended or adjusted under 35 U.S.C. 154(b) by 176 days.

(21) Appl. No.: 11/831,794

(22) Filed: Jul. 31, 2007

(65) Prior Publication Data

US 2008/0029086 A1 Feb. 7, 2008

Related U.S. Application Data

(60) Provisional application No. 60/821,517, filed on Aug. 4, 2006.

(51) Int. Cl.
*A61M 31/00* (2006.01)

(52) U.S. Cl. ........ 604/275; 604/249; 604/256; 604/246; 604/247; 604/248; 401/126; 239/323

(58) Field of Classification Search .......... 604/246–256, 604/275; 206/236–368, 420–422, 260–268; 401/126; 239/323
See application file for complete search history.

(56) References Cited

U.S. PATENT DOCUMENTS

| 4,168,032 | A * | 9/1979 | Sneider | 239/327 |
| 6,238,377 | B1 * | 5/2001 | Liu | 604/289 |
| 6,290,108 | B1 * | 9/2001 | Gross | 222/494 |
| 6,520,384 | B2 * | 2/2003 | Mehta | 222/211 |
| 6,736,792 | B1 * | 5/2004 | Liu | 604/94.01 |
| 6,745,760 | B2 | 6/2004 | Grychowski et al. | |
| 6,907,879 | B2 * | 6/2005 | Drinan et al. | 128/202.22 |
| 7,335,186 | B2 | 2/2008 | O'Neil | |
| 2002/0158089 | A1 | 10/2002 | Mehta | |
| 2002/0170928 | A1 | 11/2002 | Grychowski | |
| 2002/0190079 | A1 * | 12/2002 | Hamamoto | 222/105 |
| 2005/0121408 | A1 * | 6/2005 | Deemer et al. | 215/381 |
| 2006/0045605 | A1 * | 3/2006 | Deans et al. | 401/126 |

FOREIGN PATENT DOCUMENTS

FR 2864448 7/2005

OTHER PUBLICATIONS

Extended European Search Report dated Dec. 9, 2010 for European Application No. 07813645, pp. 1-8.

\* cited by examiner

*Primary Examiner* — Bhisma Mehta
*Assistant Examiner* — Edelmira Bosques
(74) *Attorney, Agent, or Firm* — Stephen C. Beuerle; Procopio Cory Hargreaves & Savitch LLP

(57) ABSTRACT

A nasal passage washing device includes a pliable body including an open top; and an applicator cap removably attached to the pliable body to cover and uncover the open top. The applicator cap includes an applicator tip having a substantially frustoconical configuration sized and shaped for receipt at least partially within a nostril of a user for sealing engagement therewith, the applicator tip including a hole to transfer washing solution there through, a washing solution transfer tube in communication with the hole of the applicator tip and a bottom of an inside of the pliable body to transfer washing solution from the bottom of the inside of the pliable body to the hole of the applicator tip, and a one-way air valve that only allows air flow into the pliable body through the one-way air valve and does not allow air flow and washing solution flow out of the pliable body through the one-way air valve.

17 Claims, 2 Drawing Sheets

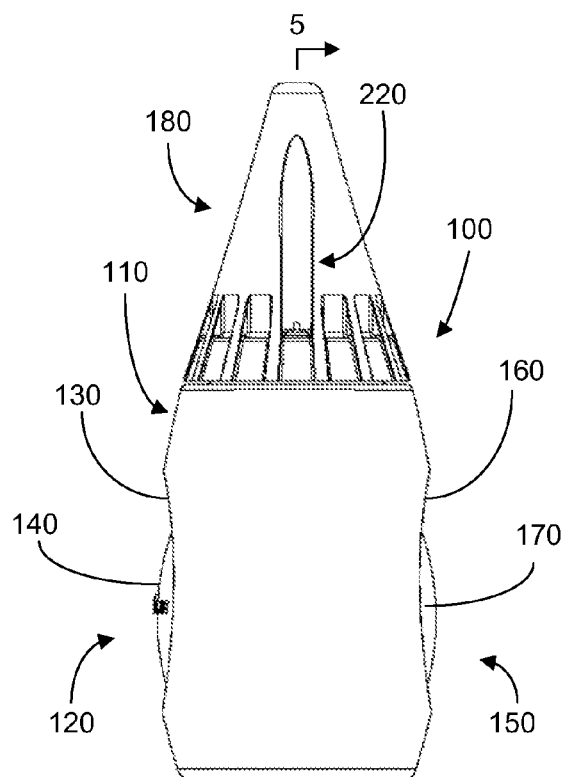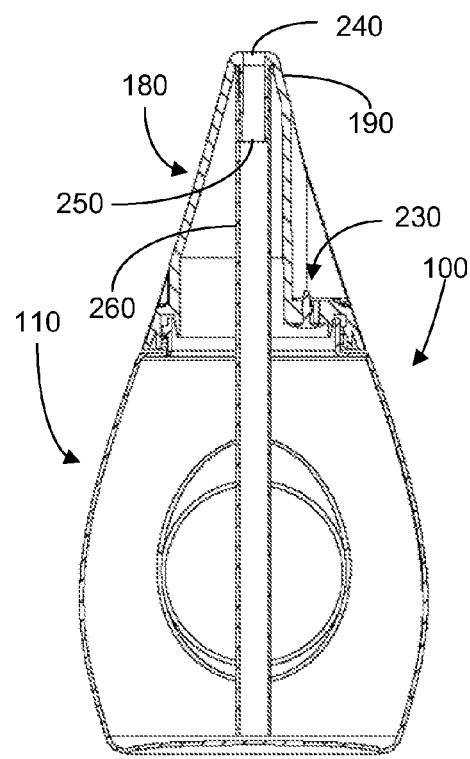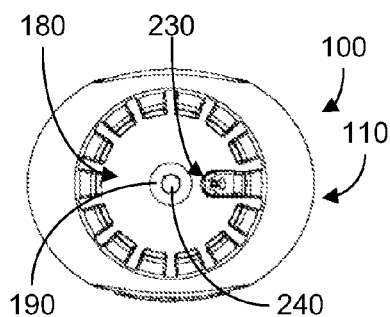
FIG. 3
FIG. 5
FIG. 4

US 8,092,434 B2

DEVICE AND METHOD FOR WASHING NASAL PASSAGES

FIELD OF THE INVENTION

The present invention is in the field of nasal wash devices and methods.

BACKGROUND OF THE INVENTION

Nasal washes have been used in the past to deliver a saline solution to a user's nasal passages (through a user's nostrils) to wash or lavage the nasal passages to relieve symptoms caused by sinus infections, allergies and the common cold, including nasal congestion, irritated nasal passages, nasal drainage, post-nasal drip, cough, and nasal headaches.

SUMMARY OF THE INVENTION

The present inventions involves a nasal wash device and method for applying a saline solution to a user's nasal passages to wash or lavage the nasal passages to relieve the above symptoms. The nasal wash device has a pliable body with a substantially tear-drop shape and a frustonconical cap. The cap has an applicator tip with a hole therein for applying a saline solution to a user's nasal passages through the user's nostrils. The pliable body is compressed to impart positive pressure within the body to cause the saline solution to be applied through the applicator tip into the nasal passages. When the pliable body is released, air enters the pliable body through an air return valve so that the body can return to its original shape without sucking air, water, and mucus back in through the applicator tip.

Another aspect of the invention involves a nasal passage washing device for washing the nasal passages of a user. The nasal passage washing device includes a pliable body to hold a nasal passage washing solution, the pliable body including an open top; and an applicator cap removably attached to the pliable body to cover and uncover the open top, the applicator cap including an applicator tip having a substantially frustoconical configuration sized and shaped for receipt at least partially within a nostril of a user for sealing engagement therewith, the applicator tip including a hole to transfer washing solution there through, a washing solution transfer tube in communication with the hole of the applicator tip and a bottom of an inside of the pliable body to transfer washing solution from the bottom of the inside of the pliable body to the to the hole of the applicator tip, and a one-way air valve that only allows air flow into the pliable body through the one-way air valve, and does not allow air flow and washing solution flow out of the pliable body through the one-way air valve.

A further aspect of the invention involves a method of using the nasal passage washing device described immediately above for washing the nasal passages of a user. The method includes a) leaning one's head over a sink; b) placing the applicator tip up to one of the user's nostrils so that the substantially frustoconical configuration of the tip forms a seal with the user's nostril ; c) applying external pressure to the pliable body by squeezing the pliable body so that nasal passage washing solution enters the user's nostril and nasal passages while the one-way air valve prevents air flow and washing solution flow out of the pliable body through the one-way valve; d) releasing the external pressure on the pliable body so that the one-way air valve allows air flow into the pliable body through the one-way valve, allowing the pliable body to return to its original shape; e) draining the nasal passage washing solution out of the user's opposite nostril, into the sink below the user's head; and f) repeating steps b-e with the user's opposite nostril.

Further objects and advantages will be apparent to those skilled in the art after a review of the drawings and the detailed description of the preferred embodiments set forth below.

BRIEF DESCRIPTION OF THE DRAWINGS

FIG. 3 is a right side elevational view of the nasal wash device illustrated in FIG. 1.

FIG. 4 is top plan view of the nasal wash device illustrated in FIG. 1.

FIG. 5 is a cross-sectional view of the nasal wash device, taken along lines 5-5 of FIG. 3.

DETAILED DESCRIPTION OF PREFERRED EMBODIMENTS

Figure 1:
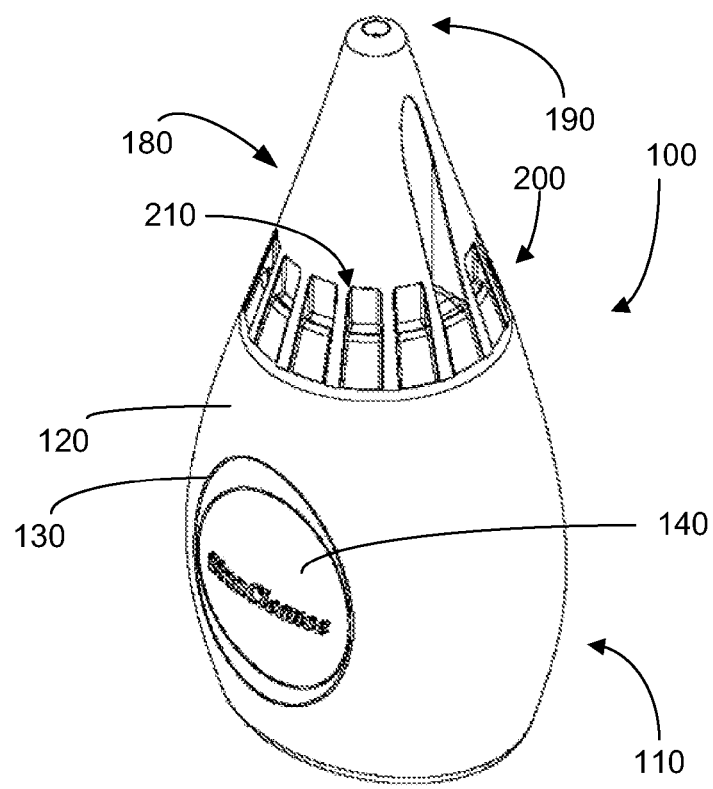
FIG. 1 is a front perspective view of a nasal wash device constructed in accordance with an embodiment of the invention.
Figure 2:
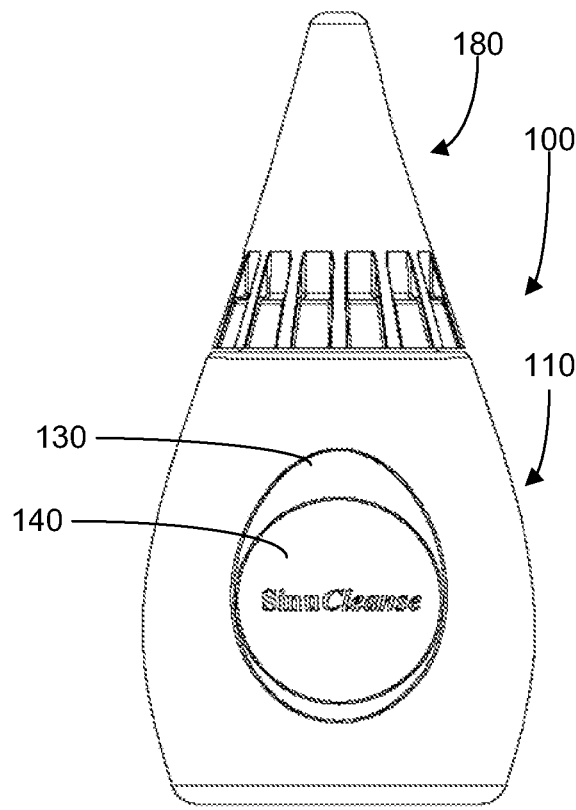
FIG. 2 is a front elevational view of the nasal wash device illustrated in FIG. 1.

With reference to FIGS. 1-5, an embodiment of a nasal wash device 100 and an exemplary method of using the nasal wash device 100 will now be described. The nasal wash device 100 will be described in conjunction with rinsing a user's nasal passages with a saline solution to wash or lavage the nasal passages to relieve symptoms caused by sinus infections, allergies, flu and the common cold, including nasal congestion, irritated nasal passages, nasal drainage, post-nasal drip, cough, and nasal headaches. This removes inhaled irritants (e.g., dust, pollen, smoke), promotes nasal and sinus drainage, and helps reduce swelling of nasal membranes. In alternative embodiments, the wash device 100 is used to wash a tissue of a user (with a saline solution or a different solution) such as, but not by way of limitation, a mucus membrane, eye tissue, and skin or tissue inside an oral cavity.

The nasal wash device 100 includes a pliable body 110 made of a flexible material (e.g., polyethelyne). The body 110 is dishwasher-safe. The body 110 has a substantial tear-drop shape. A front 120 of the pliable body 110 includes a pliable oval concave section 130 with a pliable/pressable circular bulbous member 140. A rear 150 (FIG. 3) of the pliable body 110 includes a pliable oval concave section 160 with pliable/pressable bulbous member 170. An upper crescent-shaped section and a lower crescent-shaped section are formed in the oval concave section 130, 160 between a perimeter of the oval concave section 130, 160 and a perimeter of the circular bulbous member 140, 170.

The body 110 includes an open top that is covered with a frustoconical cap 180. The cap 180 include an applicator tip 190 and a base 200 with a much larger diameter than the applicator tip 190. The base 200 includes indentations 210 along its periphery. One of the indentations 210 is an air-return indentation 220. The remaining indentations 210 have substantially the same configuration. The air-return indentation 220 extends substantially the entire vertical distance of the cap 180. At the base 200, the air-return indentation 220 includes a flat ledge, which is substantially parallel with bottom of the body 110, with an air return valve 230 (FIG. 5) therein. The air return valve 230 is a one-way air valve that allows air into the body 110 through the valve 230 (after compressing the body 110, with negative pressure in the body 110), but does not allow air or liquid out of the body 110 through the valve 230 (while compressing the body 110, with positive pressure in the body 110). The tip 190 includes an opening 240 and a downwardly protruding, cylindrical attachment portion 250. In an alternative embodiment, the cylindrical attachment portion 250 includes (or is replaced by) a one-way valve that allows liquid out of the applicator tip 190 of the cap 180 (while compressing the body 110, with positive pressure in the body 110), but prevents backflow/backwash back into the applicator tip 190 of the cap 180 (after compressing the body 110, with negative pressure in the body 110). A cylindrical tube 260 connects to the cylindrical attachment portion 250. When the cap 180 is connected to the top of the body 110, the cylindrical tube 260 extends in a longitudinal direction relative to the device 100 and terminates at a lower end near the inside, bottom of the body 110.

The nasal wash device 100 will now be described in use. The saline solution applied to the nasal passages is created first. To create the saline solution, the cap 180 is remove from the body 110, and the contents from one (1) saline solution packet, which is filled with dry saline solution ingredients, are emptied into the body 110, through the open top of the body 110. As one becomes more accustomed to the nasal wash device 100 and method of use, two (2) saline solution packets are emptied into the body 110. The body 110 is then filled with warm water (e.g., water having a temperature higher than room temperature). The cap 180 is tightened on the body 110. The user places one finger on the tip 190 of the cap 180 (or otherwise covers the tip 190 of the cap 180) and the nasal wash device 100 is gently shaken in order to ensure that the dry ingredients have completely dissolved. It is important for the user to have a proper head position during application of the saline solution to the nasal passages. The user leans over or bends over the sink with one's head bent down so that the user is looking directly into the basin. While holding the nasal wash device 100 in the user's right hand, with the user's thumb over one of the bulbous members 140,170 and adjacent finger(s) over the opposite bulbous member 140,170, the user places the tip 190 of the cap 180 up to the right nostril and gently inserts the substantially frustonconical tip 190 so that it forms a comfortable seal with the rim of the right nostril. The tip 190 is aimed toward the back of the user's head, not towards the top of the user's head. The user applies external pressure to the pliable body 110 by pressing gently on one of the bulbous members 140,170 with the user's thumb and pressing gently on the opposite bulbous member 140,170 with the user's adjacent finger(s) so that the pliable body 110 is slightly compressed (i.e., the pliable body 110 is squeezed). This imparts positive pressure in the body 110, causing the saline solution to enter the user's right nostril. In the embodiment where the cap 180 includes a one-way liquid valve, the saline solution flows out of the one-way liquid valve and out of the tip 190, and is prevented from flowing back into the wash device 100 through tip 190. Breathing should be done through one's mouth during this process and the user should not inhale or "snort" the solution into the nose. After squeezing the body 110, releasing the external pressure on the opposite bulbous member 140,170 creates negative pressure in the body 110, allowing air into the body 110 through the one-way, air return valve 230. In a few moments, the solution begins to drain out of the left nostril. The user continues squeezing the body 110 gently until approximately half of the solution in the nasal wash device 100 has been used. At this point, the user exhales through both nostrils to clear them of excess mucus and solution. The user gently blows one's nose in a tissue.

The procedure is repeated on the left nostril with the remaining solution.

Adults and children age four (4) years and older may use 1-2 saline packets administered as described above every two (2) hours. Children under age four (4) should consult a health care professional before use.

The nasal wash device 100 is thoroughly cleaned after each use.

The above description of the disclosed embodiments is provided to enable any person skilled in the art to make and use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

What is claimed is:

1. A nasal passage washing device for washing the nasal passages of a user, comprising:

a pliable body to hold a nasal passage washing solution, the pliable body including an open top, a flat bottom surface, a front including a central pliable oval section that is concave inward and a pliable circular bulbous member disposed within and directly extending from the central pliable oval section and all of pliable circular bulbous member convex outward from the central pliable oval section at a constant radius of curvature, a rear including a central pliable oval section that is concave inward and a pliable circular bulbous member disposed within and directly extending from the central pliable oval section and all of pliable circular bulbous member convex outward from the central pliable oval section at a constant radius of curvature, the central pliable oval section of the front concave inward in a direction opposite of the concave inward direction of the central pliable oval section of the rear, the pliable circular bulbous member of the front convex outward in a direction opposite of the convex outward direction of the of the pliable circular bulbous member of the rear, the oval concave section including a perimeter and the circular bulbous member including a perimeter, and an upper crescent-shaped section and a lower crescent-shaped section formed in the oval concave section between the perimeter of the oval concave section and the perimeter of the circular bulbous member; and an applicator cap removably attached to the pliable body to cover and uncover the open top, the applicator cap including an applicator tip having a substantially frustoconical configuration sized and shaped for receipt at least partially within a nostril of a user for sealing engagement therewith, the applicator tip including a hole to transfer washing solution there through, a washing solution transfer tube in communication with the hole of the applicator tip and a bottom of an inside of the pliable body to transfer washing solution from the bottom of the inside of the pliable body to the hole of the applicator tip, and at least one one-way air valve that only allows air flow into the pliable body through the one-way air valve, and does not allow air flow and washing solution flow out of the pliable body through the one-way air valve, wherein the applicator cap includes a height and also includes a circumference with indentations spaced at the circumference of the applicator cap, each indentation including a ledge that is parallel to the flat bottom surface of the pliable body, and further wherein at least one of the indentations is an air-return indentation, the air-return indentation being taller than the rest of the indentations but shorter than the applicator cap, and further wherein the one-way air valve is positioned within the ledge of the air-return indentation.

2. The nasal passage washing device of claim 1, wherein the pliable body has a substantial tear-drop shape.

3. The nasal passage washing device of claim 1, wherein the applicator cap includes a one-way anti-backwash valve that allows washing solution flow out of the applicator cap through the one-way anti-backwash valve and prevents liquid flow into the applicator cap one-way anti-backwash valve.

4. The nasal passage washing device of claim 1, wherein the at least one-way air valve is positioned within the ledge of at least one of the indentations that are not the air-return indentation.

5. The nasal passage washing device of claim 1, wherein the applicator cap includes a base, and the applicator cap is substantially frustoconical and inclined at a constant angle from the base to the applicator tip, the pliable body including a top portion with sides inclined at an angle, the base of the applicator cap adjacent to the top portion of the pliable body, and the angle of the sides of the top portion of the pliable body being the same as the constant angle from the base to the applicator tip of the applicator cap.

6. The nasal passage washing device of claim 1, further including multiple saline dry ingredient packages adapted to be mixed with warm water above room temperature to form the washing solution in the nasal passage washing device.

7. A method of using a nasal passage washing device for washing the nasal passages of a user, the nasal passage washing device including a pliable body including a nasal passage washing solution, the pliable body including an open top, a flat bottom surface, a front including a central pliable oval section that is concave inward and a pliable circular bulbous member disposed within and directly extending from the central pliable oval section and all of pliable circular bulbous member convex outward from the central pliable oval section at a constant radius of curvature, a rear including a central pliable oval section that is concave inward and a pliable circular bulbous member disposed within and directly extending from the central pliable oval section and all of pliable circular bulbous member convex outward from the central pliable oval section at a constant radius of curvature, the central pliable oval section of the front concave inward in a direction opposite of the concave inward direction of the central pliable oval section of the rear, the pliable circular bulbous member of the front convex outward in a direction opposite of the convex outward direction of the pliable circular bulbous member of the rear, the oval concave section including a perimeter and the circular bulbous member including a perimeter, and an upper crescent-shaped section and a lower crescent-shaped section formed in the oval concave section between the perimeter of the oval concave section and the perimeter of the circular bulbous member; an applicator cap removably attached to the pliable body to cover and uncover the open top, the applicator cap including an applicator tip having a substantially frustoconical configuration sized and shaped for receipt at least partially within a nostril of a user for sealing engagement therewith, the applicator tip including a hole to transfer washing solution there through, a washing solution transfer tube in communication with the hole of the applicator tip and a bottom of an inside of the pliable body to transfer washing solution from the bottom of the inside of the pliable body to the hole of the applicator tip, and at least one one-way air valve that only allows air flow into the pliable body through the one-way air valve, and does not allow air flow and washing solution flow out of the pliable body through the one-way air valve, the applicator cap including a height and also a circumference with indentations spaced at the circumference of the applicator cap, each indentation including a ledge that is parallel to the flat bottom surface of the pliable body, and wherein at least one of the indentations is an air-return indentation, the air-return being taller than the rest of the indentations but shorter than the applicator cap, and further wherein the one-way air valve is positioned within the ledge of the air-return indentation, comprising:

a) leaning one's head over a sink;
b) placing the applicator tip up to one of the user's nostrils so that the substantially frustoconical configuration of the tip forms a seal with the user's nostril;
c) applying external pressure to the pliable body by squeezing the pliable circular bulbous member of the front and the pliable circular bulbous member of the rear of the pliable body so that nasal passage washing solution enters the user's nostril and nasal passages while the one-way air valve prevents air flow and washing solution flow out of the pliable body through the one-way air valve;
d) releasing the external pressure on the pliable body so that one-way air valve allows air flow into the pliable body through the one-way air valve, allowing the pliable body to return to its original shape;
e) draining the nasal passage washing solution out of the user's opposite nostril, into the sink below the user's head;
f) releasing the external pressure on the pliable body so that the one-way air valve allows air flow into the pliable body, allowing the pliable body to return to its original shape;
g) repeating steps b-f with the user's opposite nostril.

8. The method of claim 7, further including removing the applicator cap from the pliable body, adding warm water above room temperature and a saline dry ingredient composition to the pliable body, attaching the applicator cap to the pliable body, covering at least the hole of the applicator tip, and shaking the nasal passage washing device until the saline dry ingredient has completely dissolved.

9. The method of claim 7, further including leaning one's head over the sink so that the user is looking directly into the basin of the sink and placing the applicator tip up to one of the user's nostrils includes placing the applicator tip up to one of the user's nostrils with the applicator tip aimed at the back of the user's head.

10. The method of claim 7, further including breathing through one's mouth during the method, removing the nasal passage washing device from one's nostril after completion, and exhaling through one's nostrils to clear them of excess mucous and nasal passage washing solution.

11. The method of claim 7, wherein the pliable body has a substantial tear-drop shape and applying external pressure to the pliable body includes applying external pressure to the substantial tear-drop shape pliable body.

12. The method of claim 7, wherein the one-way air valve is positioned within the ledge of one of the indentations that is not an air-return indentation.

13. The method of claim 7, wherein the applicator cap includes a one-way anti-backwash valve that allows washing solution flow out of the applicator cap and prevents liquid flow into the applicator cap, and applying external pressure to the pliable body so that the one-way anti-backwash valve allows washing solution flow out of the applicator cap and prevents liquid flow into the applicator cap.

14. The method of claim 7, wherein pliable body includes a bottom and the applicator cap includes a ledge parallel with the bottom of the pliable body, and the ledge includes the one-way air valve therein, and releasing the external pressure on the pliable body so that the one-way air valve allows air flow into the pliable body, allowing the pliable body to return to its original shape.

15. The method of claim 7, wherein the applicator cap includes a base, and the applicator cap is substantially frustoconical and inclined at a constant angle from the base to the applicator tip, the pliable body including a top portion with sides inclined at an angle, the base of the applicator cap adjacent to the top portion of the pliable body, and the angle of the sides of the top portion of the pliable body being the same as the constant angle from the base to the applicator tip of the applicator cap, and placing the applicator tip of the substantially frustoconical applicator cap up to one of the user's nostrils so that the substantially frustoconical configuration of the tip forms a seal with the user's nostril.

16. A method of using a nasal passage washing device for washing the nasal passages of a user, the nasal passage washing device including a pliable body including a nasal passage washing solution, the pliable body including an open top, a flat bottom surface, a front including a central pliable oval section that is concave inward and a pliable circular bulbous member disposed within and directly extending from the central pliable oval section and all of pliable circular bulbous member convex outward from the central pliable oval section at a constant radius of curvature, a rear including a central pliable oval section that is concave inward and a pliable circular bulbous member disposed within and directly extending from the central pliable oval section and all of pliable circular bulbous member convex outward from the central pliable oval section at a constant radius of curvature, the central pliable oval section of the front concave inward in a direction opposite of the concave inward direction of the central pliable oval section of the rear, the pliable circular bulbous member of the front convex outward in a direction opposite of the convex outward direction of the of the pliable circular bulbous member of the rear, the oval concave section including a perimeter and the circular bulbous member including a perimeter, and an upper crescent-shaped section and a lower crescent-shaped section formed in the oval concave section between the perimeter of the oval concave section and the perimeter of the circular bulbous member; an applicator cap removably attached to the pliable body to cover and uncover the open top, the applicator cap including a circumference with indentations spaced at the circumference of the applicator cap, each indentation including a ledge that is parallel to the flat bottom surface of the pliable body, and wherein at least one of the indentations is an air-return indentation, the air-return indentation being taller than the rest of the indentations but shorter than the applicator cap, the applicator cap including an applicator tip having a substantially frustoconical configuration sized and shaped for receipt at least partially within a nostril of a user for sealing engagement therewith, the applicator tip including a hole to transfer washing solution there through, a washing solution transfer tube in communication with the hole of the applicator tip and a bottom of an inside of the pliable body to transfer washing solution from the bottom of the inside of the pliable body to the hole of the applicator tip, and at least one one-way air valve that only allows air flow into the pliable body through the one-way air valve, and does not allow air flow and washing solution flow out of the pliable body through the one-way air valve and wherein the one-way air valve is positioned within the ledge of the air-return indentation, the applicator cap including a base and being substantially frustoconical and inclined at a constant angle from the base to the applicator tip, the pliable body including a top portion with sides inclined at an angle, the base of the applicator cap being adjacent to the top portion of the pliable body, and the angle of the sides of the top portion of the pliable body being the same as the constant angle from the base to the applicator tip of the applicator cap, comprising:
  a) leaning one's head over a sink;
  b) placing the applicator tip up to one of the user's nostrils so that the substantially frustoconical configuration of the tip forms a seal with the user's nostril;
  c) applying external pressure to the pliable body by squeezing the pliable circular bulbous member of the front and the pliable circular bulbous member of the rear of the pliable body so that nasal passage washing solution enters the user's nostril and nasal passages while the one-way air valve presents air flow and washing solution flow out of the pliable body through the one-way air valve;
  d) releasing the external pressure on the pliable body so that one-way air valve allows air flow into the pliable body through the one-way air valve, allowing the pliable body to return to its original shape;
  e) draining the nasal passage washing solution out of the user's opposite nostril, into the sink below the user's head;
  f) releasing the external pressure on the pliable body so that the one-way air valve allows air flow into the pliable body, allowing the pliable body to return to its original shape;
  g) repeating steps b-f with the user's opposite nostril.

17. The method of claim 16, wherein the one-way air valve is positioned within the ledge of one of the indentations that is not an air-return indentation.

* * * * *